(12) United States Patent
Wheeler

(10) Patent No.: US 7,927,281 B2
(45) Date of Patent: Apr. 19, 2011

(54) AUTOMATED NEEDLE PEN DRUG DELIVERY SYSTEM

(76) Inventor: Jay Wheeler, Tulsa, OK (US)

( * ) Notice: Subject to any disclaimer, the term of this patent is extended or adjusted under 35 U.S.C. 154(b) by 29 days.

(21) Appl. No.: 12/247,740

(22) Filed: Oct. 8, 2008

(65) Prior Publication Data

US 2009/0093762 A1    Apr. 9, 2009

Related U.S. Application Data

(60) Provisional application No. 60/978,169, filed on Oct. 8, 2007, provisional application No. 61/055,041, filed on May 21, 2008.

(51) Int. Cl.
*A61B 8/14* (2006.01)
(52) U.S. Cl. ........................ 600/459; 604/176
(58) Field of Classification Search .... 604/95.01–95.05, 604/113–119, 174–180, 523–532; 600/423, 600/424, 459, 462
See application file for complete search history.

(56) References Cited

U.S. PATENT DOCUMENTS

| 3,682,162 | A | | 8/1972 | Colyer | |
|---|---|---|---|---|---|
| 5,180,371 | A | | 1/1993 | Spinello | |
| 5,830,151 | A | | 11/1998 | Hadzic et al. | |
| 6,139,571 | A | * | 10/2000 | Fuller et al. | 607/105 |
| 6,171,251 | B1 | * | 1/2001 | Mueller et al. | 600/481 |
| 6,533,732 | B1 | | 3/2003 | Urmey | |
| 6,678,550 | B2 | | 1/2004 | Hubbard, Jr. | |
| 6,706,016 | B2 | | 3/2004 | Cory et al. | |
| 6,866,648 | B2 | | 3/2005 | Hadzic et al. | |
| 6,973,346 | B2 | | 12/2005 | Hafer et al. | |
| 7,047,085 | B2 | | 5/2006 | Cory et al. | |
| 7,120,487 | B2 | | 10/2006 | Nelson | |
| 2003/0014037 | A1 | * | 1/2003 | Thompson et al. | 604/528 |
| 2003/0167021 | A1 | * | 9/2003 | Shimm | 600/554 |
| 2006/0084911 | A1 | * | 4/2006 | Belef et al. | 604/95.01 |

* cited by examiner

*Primary Examiner* — Nicholas D Lucchesi
*Assistant Examiner* — Gerald Landry, II
(74) *Attorney, Agent, or Firm* — Fellers, Snider, Blankenship, Bailey & Tippens, P.C.

(57) ABSTRACT

A drug delivery system utilizes a hand piece adapted to receive a probe. The hand piece may be made of a first segment and a second segment connected to one another by a swivel joint to accommodate a user's position and preference for switches provided thereon. Alternatively, the switches may be mounted on rotatable bases. A base unit connected to the hand piece delivers a substance to the hand piece via a drug line. The base unit may further include a nerve stimulator for transmitting current to the probe. A drug switch on the hand piece selectively activates a drug delivery and suction to facilitate aspiration. A current switch on the hand piece selectively delivers electric current to the probe. In practice, the hand piece of the invention may be used by a single operator operating an ultrasound wand with a first hand and operating the hand piece with a second hand, thereby reducing personnel typically required to perform certain tasks.

10 Claims, 4 Drawing Sheets

AUTOMATED NEEDLE PEN DRUG DELIVERY SYSTEM

CROSS REFERENCE TO RELATED APPLICATIONS

This application claims the priority of U.S. Provisional Patent Application No. 60/978,169 entitled "AUTOMATED NEEDLE PEN DRUG DELIVERY SYSTEM," filed Oct. 8, 2007, and U.S. Provisional Patent Application No. 61/055, 041 entitled "AUTOMATED NEEDLE PEN DRUG DELIVERY SYSTEM," filed May 21, 2008, the contents of which are hereby incorporated by reference.

FIELD OF THE INVENTION

The invention relates generally to the field of automated needle pen drug delivery systems for delivering substances to a patient. More particularly, but not by way of limitation, the invention relates to an automated needle pen having features that allow a practitioner to selectively aspirate, inject, and perform additional functions.

BACKGROUND OF THE INVENTION

Substances such as medications, contrast media, and local anesthetics have been administered for various clinical situations including implantable pain medication/insulin pumps, interventional radiological and cardiologic procedures, acute perioperative and chronic pain blocks. Historically, such procedures have been performed using a two-man approach. Because of technological limitations, a first person, operating in a sterile field, identified and isolated a patient's structure with a needle or probe. A second person was required to inject the substance from a nonsterile site through a tube into the apparatus held by the first person.

To reduce costs, minimize the potential for problems arising from miscommunication, and reduce manpower requirements, it is desirable for such procedures to be implemented by a single person rather than by two people.

SUMMARY OF THE INVENTION

The invention of the present disclosure, in one aspect thereof, comprises a drug delivery device. The device includes a hand piece having first and second ends, a joint connecting the first and second ends, a first selective switch on the first end, and a second selective switch on the second end. The first end of the hand piece interconnects with a base unit to receive an injectate from the base unit dependent upon a position of the second selective switch and to receive a current from the base unit dependent on a position of the first selective switch. The second end of the hand piece provides the injectate and current to the probe.

The first end of the hand piece further selectively receives vacuum from the base unit to be drawn through the probe based upon the position of the second selective switch. The hand piece may also provide data to the base unit. The system may also utilize a combination data and current line for receiving current from the base unit and for delivering data to the base unit.

In some embodiments, the system has a first rotatable base connecting the first switch to the first end of the hand piece. A second rotatable base may connect the second switch to the second end of the hand piece. The first and second rotatable bases may have a limited degree of rotation and may have an internal detent mechanism. The joint between the first and second ends may be a friction joint and may have an internal detent mechanism.

The system may have a base unit connecting to the first end of the hand piece and a probe connecting to the second end of the hand piece. The base unit selectively provides injectate or vacuum to the probe via the hand piece based upon a selection of the second switch and provides electrical current to the probe via the hand piece based upon a selection of the first switch.

The automated needle pen drug delivery system (ANP system) enables the administration of medications, contrast media, local anesthetics, and other procedures to be performed by one individual, rather than two, thus minimizing the potential for problems arising from miscommunication. The ANP system also facilitates more efficient and cost effective treatment.

In one embodiment, the ANP system utilizes a hand piece or pen that may be attached to various types of needles and probes. In some embodiments, the hand piece may be a single use, sterile, disposable type. The hand piece may be pen-shaped and roughly the size of a cigar. A switch, such as a toggle switch, may be located at approximately the distal end of the hand piece. The switch, when depressed in a first direction, e.g. proximally, activates a suction pressure, e.g. 5 psi, to a line for aspiration. Other types of switches may also be used for this and other applications within the present disclosure. These include, without limitation, adjacent buttons, capacitive contact switches, membrane switches, spring loaded buttons, or other types of switches.

Aspiration may be used to determine whether the needle or probe tip is intravascular. Intravascular tip confirmation is essential prior to injection of contrast media as well as when injecting various local anesthetics. If the tip of the needle or probe is not in the lumen of the appropriate vascular structure, the contrast study will be meaningless. Likewise, with various pain blocks, the risk of an inadvertent intravascular injection of local anesthetic and the resulting systemic reactions can be minimized by confirmation that the tip of the needle or probe is not resting in the vessel.

When the switch is pressed in a second direction, e.g. toward a distal end, the device delivers a given volume, e.g. 5 milliliters, through the system. Therefore, the common approach of injecting and re-aspirating after each small bolus of injectate can be easily accomplished by toggling the switch. In a preferred embodiment, the device will inject with a continuous pressure of 15 psi when the distal end of the toggle switch is depressed.

A second switch may be provided which, when depressed, controls the current amplitude of a nerve stimulator connected to the system. The nerve stimulator technique is a commonly employed method of identifying nerve structures. The technique has been the standard of care in the past and will continue to be used in concert with ultrasound guided techniques in the future. The toggle switch is connected to a rheostat that controls the electrical current in the same fashion as the inject toggle switch. The nerve stimulator frequency is preferably set at 2 Hz, although other frequencies may be used.

Some embodiments of the present disclosure will provide a joint in the body of the hand piece between the first and second switches. The joint will allow the resulting two portions of the body to be rotated relative to one another to accommodate user preference and to accommodate right handed users versus left handed users. The switches may also be attached to the hand piece with rotatable platforms. The use of rotatable platforms allows the switches to be rotated from their default positions, to at least a degree, to accommodate user preferences for both right and left handed users. Other embodiments locate the switches side-by-side to accommodate right handed or left handed users.

Various types of needles or probes may be attached to the distal end of the hand piece. Depending on the need, the hand piece may be utilized for a variety of purposes, e.g., medication administration, injection of contrast media and/or injection of local anesthetic. To utilize ultrasound guidance together with nerve stimulating techniques for nerve identification, an insulated echogenic injecting needle similar to those used in the Stimuplex® systems could be attached to the hand piece. In this manner, the device may be utilized in combination with ultrasound guided/nerve stimulator techniques wherein a single operator holds the hand piece in one hand and holds an ultrasound probe in the other. The sterile hand piece may then be connected to a base unit by wires and/or tubing extending from the proximal end of the hand piece.

Another embodiment of the invention utilizes a reusable needle pen. The distal end of the hand piece may be connected to probes or stimulating/injecting needles via a common standardized interface (e.g., Luer lock). To utilize ultrasound guidance together with nerve stimulating techniques for nerve identification, an insulated, echogenic injecting needle similar to those used in the Stimuplex® systems may be attached to the hand piece. In this manner, the device is utilized in combination with an ultrasound guided/nerve stimulator technique with a single operator holding the hand piece in one hand and holding an ultrasound probe in the other.

A base unit is provided that contains controls and displays, preferably including a display, such as an LCD screen, to display programmed information for each use. The base unit is used in conjunction with any of the above described embodiments and preferably consists of a combination of nerve stimulator and infusion pump. The preferred infusion pump has a maximum syringe size of 60 milliliters. A stand-alone ultrasound machine may be used as a separate component of the system, or may be incorporated into the pump stimulator device as one unit. Infusion tubing, together with wiring from the nerve stimulator extends from the base unit to the proximal end of the hand piece. For the reusable embodiment, a custom fitted sterile condom with a serrated removable end may be provided to fit over the Luer lock end of the hand piece. The removable end is provided to allow for connecting to probes/needles, and may be used to maintain sterility during each use.

DETAILED DESCRIPTION OF THE PREFERRED EMBODIMENTS

Figure 1:
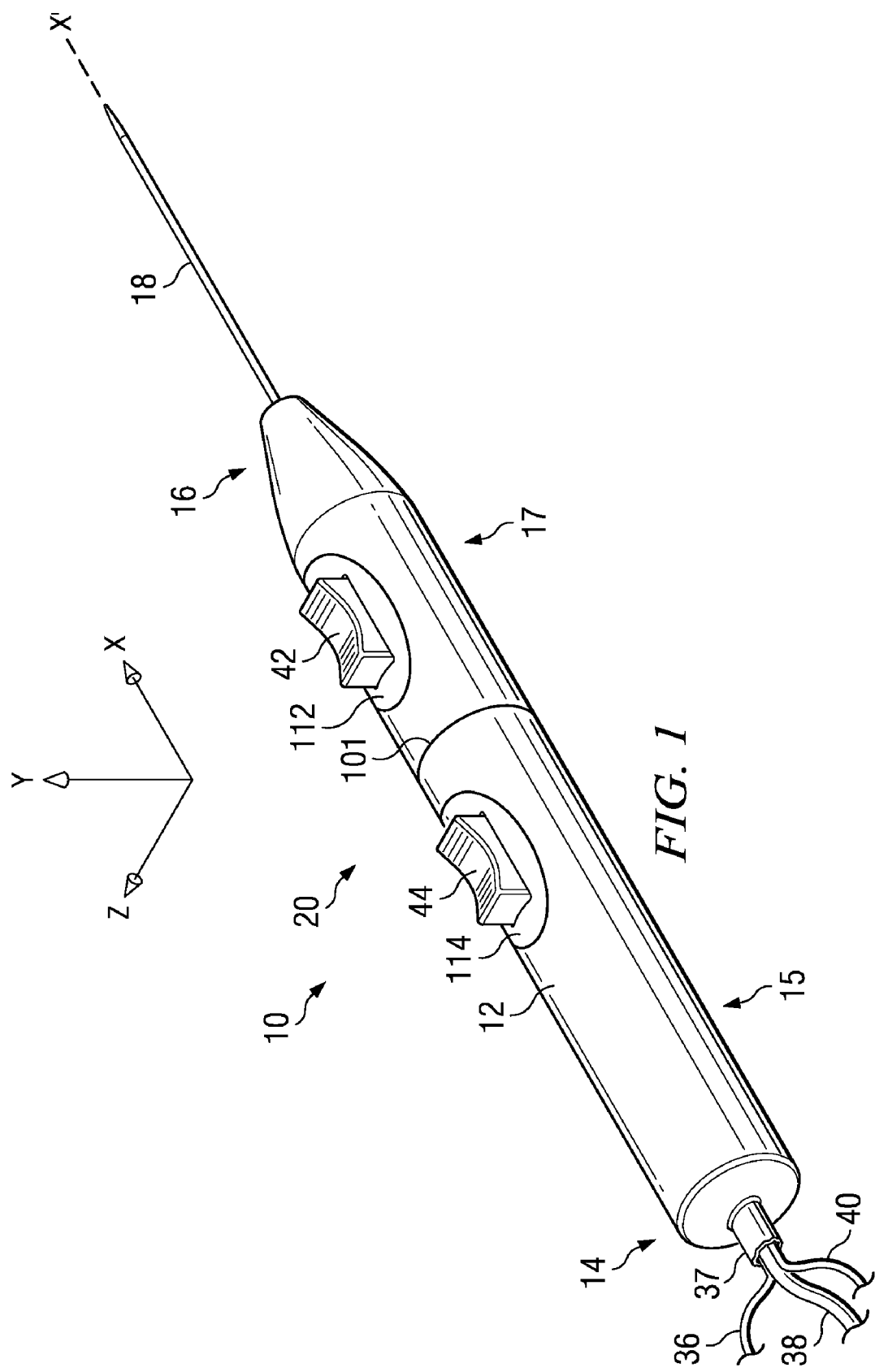
FIG. 1 is a perspective view of a disposable embodiment of the automated needle pen of the invention.
Figure 2:
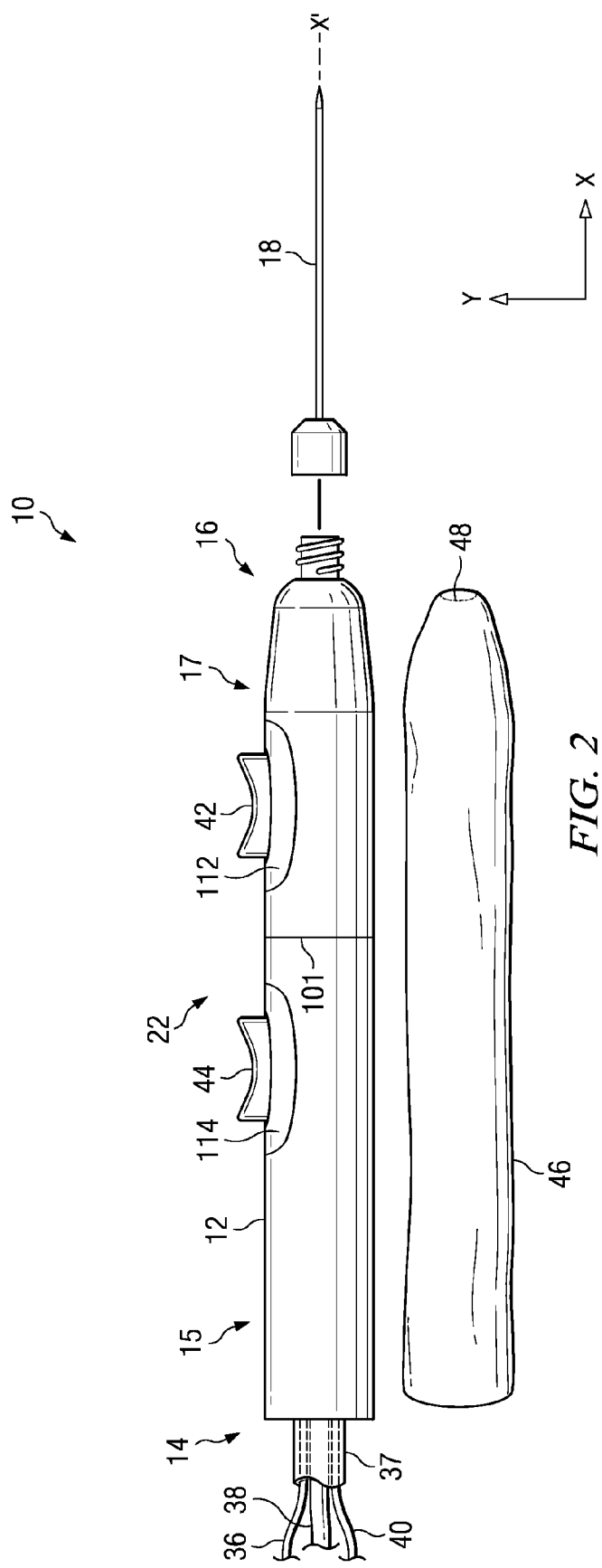
FIG. 2 is a plan view of a reusable embodiment of the automated needle pen of the present disclosure with a needle pen condom sized to be received on the needle pen of the present disclosure.

Referring now to FIGS. 1-2, shown are embodiments of an automated needle pen drug delivery system 10. Hand piece 12 has a first end 14 and a second end 16. Second end 16 is adapted to receive a probe 18, such as a needle. Hand piece 12 may be provided as a disposable embodiment 20 (FIG. 1) or as a reusable embodiment 22 (FIG. 2). In one embodiment the first end 14 is part of first segment 15 and second end 16 is part of second segment 17. First segment 15 and second segment 17 are joined together by swivel joint 101. The swivel joint 101 allows the first and second segments 15 and 17 to rotate relative to one another so as to be adjustable for the preferences of different users (e.g., right handed versus left handed users). The joint 101 may be a friction joint or may have a series of predetermined adjustments (e.g., using an internal detent mechanism)

Figure 3:
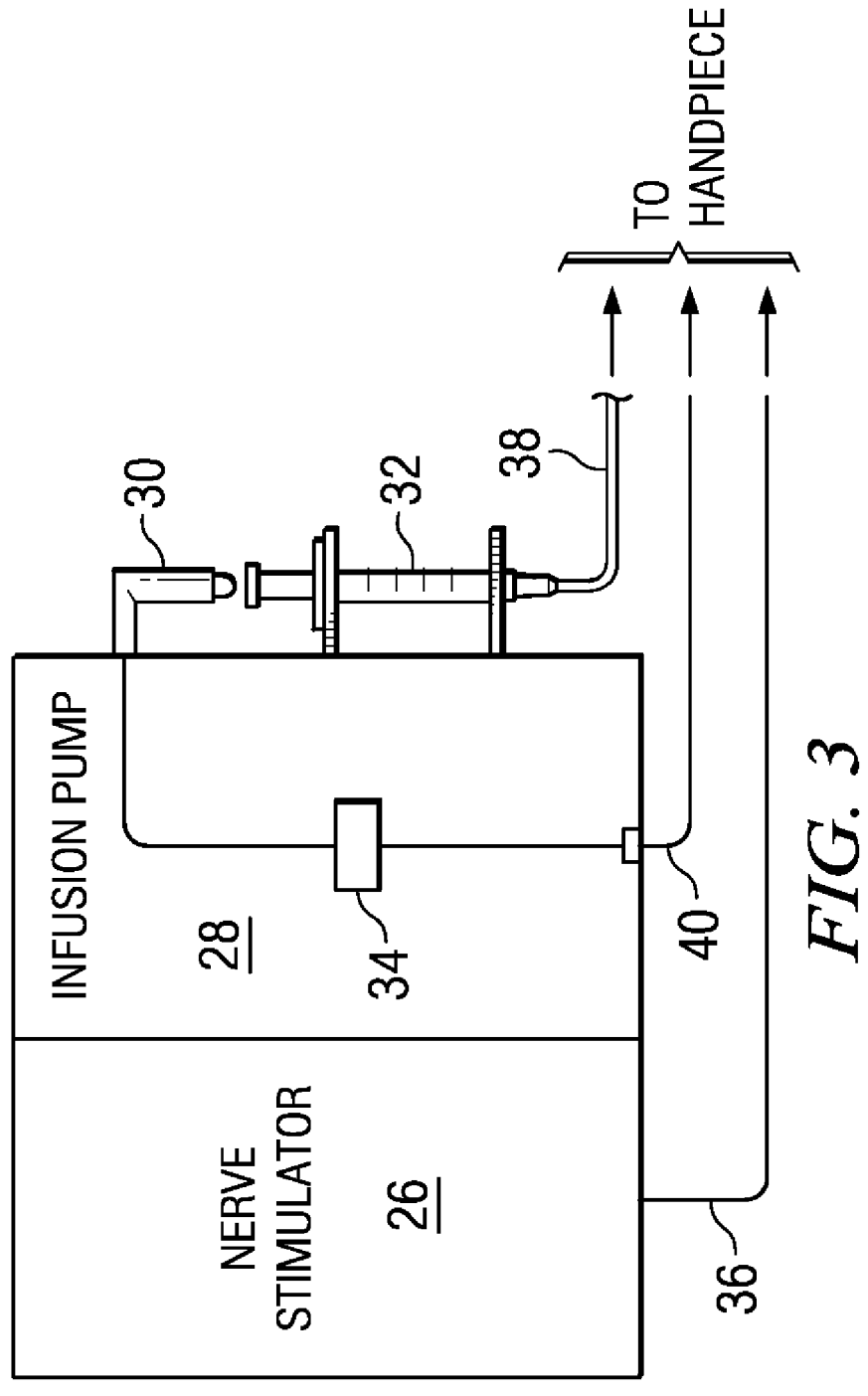
FIG. 3 is a schematic representation of a base unit for use in conjunction with the automated needle pen of FIG. 1 or FIG. 2.

A base unit 24 (FIG. 3) is provided having a nerve stimulator 26 and an infusion pump 28 that controls a plunger apparatus 30. Base unit 24 is for use with either of embodiment 20 or 22. Infusion pump 28 includes a syringe 32 and a processor 34 for controlling plunger apparatus 30. Syringe 32 preferably has a maximum size of 60 milliliters, although other sized syringes are contemplated for use with the invention.

Various lines extend from base unit 24 to first end 14 of hand piece 12. These lines may include a current line 36 that extends from nerve stimulator 26 of base unit 24, a drug line 38 that extends from syringe 32, and a data line 40 that extends from processor 34 of infusion pump 28. The data line 40 may be used for transmitting data regarding volume of injectate from hand piece 12 to processor 34. FIGS. 1 and 2 illustrate each of the three lines, i.e., current line 36, drug line 38, and data line 40 connecting to the first end 14 of the hand piece 12. In one embodiment the current lines 36, data lines 40, and tubing may be combined into a single combined line 37.

A drug switch 42, e.g., a toggle switch, is provided on hand piece 12. Although toggle switches are shown and discussed in the application, it should be understood that other types of switches may also be used. When drug switch 42 is moved to a first position, i.e., depressed in a first direction, preferably proximally, a suction pressure, e.g. 5 psi, is applied to drug line 38. When drug switch 42 is moved to a second position, i.e., depressed in a second direction, preferably toward a distal end, a given volume, e.g. 5 mL, is delivered through drug line 38 at a desired pressure. An example pressure is 15 psi.

As shown in FIGS. 1 and 2, drug switch 42 may be mounted on a rotatable base 112 on hand piece 12. Rotatable base 112 allows for the drug switch 42 to be selectively rotated about the Y axis. Rotatable 112 base may be provided with a limited degree of freedom of rotation such that drug switch 42 cannot be rotated to such a degree that its function (e.g., direction) could become confusing to a user. A preferred limit is 45° to either side of the longitudinal, or X, axis. Rotatable base 112 may be sufficiently held in a predetermined position by a friction fit, or may feature a number of predefined positions that may be selected with the assistance of an internal detent mechanism.

A second switch 44, e.g., current toggle switch 44, is additionally preferably provided on hand piece 12 for selectively delivering a current, e.g. 2 Hz, to probe 18 over current line 36, or combined line 37. Current switch 44 may also be mounted on a rotatable base 114 on the hand piece 12. Rotatable base 114 allows for the current switch 44 to be selectively rotated about the Y axis. Here again, rotatable 114 base may be provided with limited freedom of rotation such that current switch 44 cannot be rotated to such a degree that its function (e.g., direction) could become confusing to a user. A preferred limit is 45° to either side of the longitudinal, or X, axis. As with rotatable base 112, the rotatable base 114 may be sufficiently held in a predetermine position by a friction fit, or may feature a number of predefined positions that may be selected with assistance from an internal detent mechanism.

Figure 4:
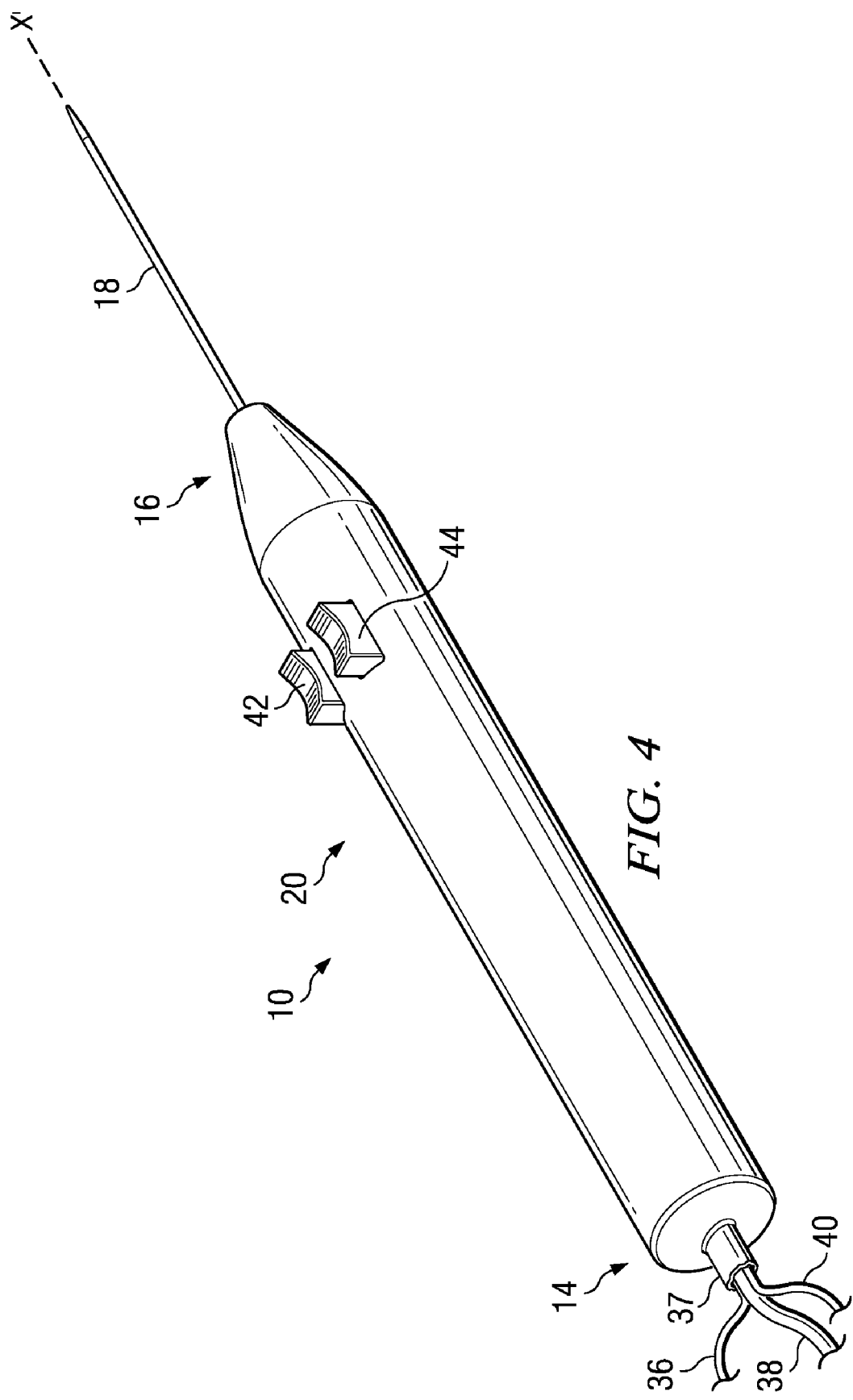
FIG. 4 is a perspective view of another embodiment of the automated needle pen of the invention.

Referring now to FIG. 4, an additional embodiment is shown wherein switches 42, 44 are located side-by-side to accommodate both left handed and right handed users.

Although the present embodiments have been described with toggle switches, used to selectively apply suction or deliver injectate, as well as select current, it should be understood that any type of single switch or multiple switches may be used to select the desired actions. Switches that may be used with various embodiments of the present disclosure include, but are not limited to, slide switches, spring loaded button switches, capacitive contact switches, optical switches, membrane switches, or other switches suitable to the environment in which the hand piece 12 is being utilized.

In some embodiments, a condom 46 (FIG. 2) is provided to cover hand piece 12. Condom 46 may be provided with a removable end 48 to facilitate attachment of probe 18 to second end 16 of hand piece 12.

The automated needle pen drug delivery system 10 of the invention may be utilized by a single practitioner. For example, the practitioner may utilize an ultrasound in one hand and the hand piece 12 in the other hand. The practitioner may also control hand piece 12 in one hand, using the various functions of the device to ensure desired placement as well as delivery of an injectate. By providing easy single hand access to drug switch 42 and current switch 44, the practitioner can aspirate, deliver drugs through drug line 38, or deliver a current to probe 18 via current line 36. Therefore, a single practitioner may administer medications, contrast media, local anesthetics, or other substances to a patient for various clinical situations including implantable pain medication/insulin pumps, interventional radiological and cardiologic procedures to acute perioperative and chronic pain blocks.

Thus, the present invention is well adapted to carry out the objectives and attain the ends and advantages mentioned above as well as those inherent therein. While presently preferred embodiments have been described for purposes of this disclosure, numerous changes and modifications will be apparent to those of ordinary skill in the art. Such changes and modifications are encompassed within the spirit of this invention as defined by the claims.

What is claimed is:

1. A drug delivery system comprising:
   a base unit having an infusion pump with a processor and a nerve stimulator having a frequency of approximately 2 Hz;
   a hand piece having a first end and a second end, the first end adapted to connect to the base unit having the infusion pump, and the second end adapted to received a probe;
   a first selective switch on the hand piece that functions to provide an electrical current from the base unit to said probe received on said second end;
   a second selective switch on the hand piece that functions to provide an injectate from the infusion pump to the received probe;
   further comprising a plurality of lines connecting the base unit and the hand piece;
   wherein the plurality of lines includes a drug line, a data line that extends from said processor of said infusion pump, and a current line that extends from said nerve stimulator of said base unit.

2. The system of claim 1, wherein said hand piece is comprised of a first segment and a second segment connected together by a swivel joint.

3. The system of claim 1, wherein the plurality of lines includes a combination current line and data line.

4. The system of claim 1, wherein said probe is a hypodermic needle.

5. A drug delivery system comprising:
   a hand piece having a first end and a second end, the first end adapted to connect to a base unit having an infusion pump, and the second end adapted to received a probe;
   a first selective switch on the hand piece that functions to provide an electrical current from the base unit to said probe received on said second end;
   a second selective switch on the hand piece that functions to provide an injectate from the infusion pump to the received probe; and
   first and second rotatable bases rotatably affixed to said hand piece, said first and second rotatable bases for receiving the first and second switches for allowing the first and second switches to rotate a predetermined degree for accommodating a position preference of a user.

6. A drug delivery device comprising:
   a hand piece having first and second ends;
   a probe affixed to said second end;
   a first selective switch on the first end;
   a second selective switch on the second end;
   a base unit in communication with said hand piece;
   wherein the first end of the hand piece interconnects with said base unit to receive an electrical current from the base unit dependent upon a position of the first selective switch and to receive an injectate from the base unit dependent on a position of the second selective switch;
   wherein the second end of the hand piece provides the injectate and current to said probe; and
   a first rotatable base connecting the first switch to the hand piece.

7. The system of claim 6, further comprising a second rotatable base connecting the second switch to the hand piece.

8. The system of claim 7, wherein the first and second rotatable bases have a limited degree of rotation.

9. A drug delivery and electrical stimulation system comprising:
   a hand piece having first and second segments, the first segment having a first switch and the second segment having a second switch;
   a base unit connecting to the first segment of the hand piece;
   a probe connecting to the second segment of the hand piece;
   wherein the base unit provides electrical current to the probe via the hand piece based upon a selection of the first switch; and
   wherein the base unit provides injectate or vacuum to the probe via the hand piece based upon a selection of the second switch; and
   further comprising first and second rotatable bases connecting the first and second switches to the first and second respective segments of the hand piece.

10. The system of claim 9, wherein the first and second segment of the hand piece are joined by a swivel connection.

* * * * *